(12) United States Patent
Ouzounov et al.

(10) Patent No.: US 10,313,027 B2
(45) Date of Patent: Jun. 4, 2019

(54) WIDE BAND THROUGH-BODY ULTRASONIC COMMUNICATION SYSTEM

(71) Applicant: KONINKLIJKE PHILIPS N.V., Eindhoven (NL)

(72) Inventors: Sotir Filipov Ouzounov, Eindhoven (NL); Neil Francis Joye, Eindhoven (NL); Christianus Martinus Van Heesch, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/507,774

(22) PCT Filed: Sep. 2, 2015

(86) PCT No.: PCT/EP2015/070013
§ 371 (c)(1),
(2) Date: Mar. 1, 2017

(87) PCT Pub. No.: WO2016/037912
PCT Pub. Date: Mar. 17, 2016

(65) Prior Publication Data
US 2017/0257175 A1 Sep. 7, 2017

(30) Foreign Application Priority Data
Sep. 11, 2014 (EP) .................................... 14184338

(51) Int. Cl.
*H04B 11/00* (2006.01)
*A61N 1/372* (2006.01)
(Continued)

(52) U.S. Cl.
CPC ............ *H04B 11/00* (2013.01); *A61B 5/0028* (2013.01); *A61B 8/12* (2013.01); *A61N 1/37217* (2013.01);
(Continued)

(58) Field of Classification Search
CPC ...................................................... H04B 11/00
See application file for complete search history.

(56) References Cited

U.S. PATENT DOCUMENTS 6,141,588 A 10/2000 Cox
6,328,697 B1 12/2001 Fraser
(Continued)

FOREIGN PATENT DOCUMENTS

| WO | 2006069215 A2 | 6/2006 |
|---|---|---|
| WO | WO 2006/069215 | * 6/2006 |

(Continued)

OTHER PUBLICATIONS

B. C. Towe, P. J. Larson, and D. W. Gulick, "Wireless ultrasound-powered biotelemetry for implants," in Proc. IEEE EMBS conference, Sep. 2-6, 2009, pp. 5421-5424.
(Continued)

*Primary Examiner* — Nay A Maung
*Assistant Examiner* — Angelica M Perez (57) ABSTRACT

A wide band through-body communication system communicates data through the body ultrasonically. A MEMS device such as a CMUT transducer is configured to transmit and/or receive ultrasonic data signals within a broad band of operating frequencies. The transducer transmits the ultrasonic data signals through the body to a similarly configured ultrasonic receiver, and/or receives ultrasonic data signals which have been conveyed through the body from a similarly configured ultrasonic transmitter for decoding and processing. In a preferred implementation a CMUT transducer is operated in a collapsed mode.

14 Claims, 6 Drawing Sheets

(51) Int. Cl.
*A61B 5/00* (2006.01)
*B06B 1/02* (2006.01)
*G10K 11/18* (2006.01)
*A61B 8/12* (2006.01)
*H03H 9/00* (2006.01)

(52) U.S. Cl.
CPC ........ *A61N 1/37288* (2013.01); *B06B 1/0207* (2013.01); *B06B 1/0292* (2013.01); *G10K 11/18* (2013.01); *H03H 9/0004* (2013.01)

(56) References Cited

U.S. PATENT DOCUMENTS

| | | |
|---|---|---|
| 7,444,185 B1 | 10/2008 | Faltys et al. |
| 8,157,740 B2 | 4/2012 | Adachi et al. |
| 9,117,438 B2 | 8/2015 | Dirksen |
| 9,539,854 B2 | 1/2017 | Klootvvijk et al. |
| 2003/0158584 A1 | 8/2003 | Cates et al. |
| 2009/0192572 A1 | 7/2009 | Dal Molin |
| 2012/0010538 A1 | 1/2012 | Dirksen et al. |
| 2012/0065458 A1 | 3/2012 | Tol et al. |
| 2012/0300593 A1 | 11/2012 | Perry |
| 2013/0087867 A1* | 4/2013 | Ho .................... B06B 1/0292 257/419 |
| 2013/0178915 A1 | 7/2013 | Radziemski et al. |
| 2014/0031694 A1* | 1/2014 | Solek ................ A61B 8/4494 600/459 |
| 2014/0187960 A1* | 7/2014 | Corl .................... A61B 8/12 600/466 |
| 2014/0247698 A1 | 9/2014 | Dirksen |
| 2016/0055305 A1* | 2/2016 | Hiriyannaiah ...... G06F 19/3418 348/14.13 |

FOREIGN PATENT DOCUMENTS

| | | | |
|---|---|---|---|
| WO | 2008011570 A1 | | 1/2008 |
| WO | WO 2008/011570 | * | 1/2008 |
| WO | 2010049842 A1 | | 5/2010 |

OTHER PUBLICATIONS

F. Mazzilli et al., "In-vitro platform to study ultrasound as source for wireless energy transfer and communication for implantable medical devices," in Proc. IEEE EMBS conference, Aug. 31-Sep. 4, 2010, pp. 3751-3754.

J.-Y. Tsai et al., "Ultrasonic wireless power and data communication for neural stimulation," in Proc. IEEE International Ultrasonics Symposium 2011, pp. 1052-1055.

Y.-S. Luo et al.,"Ultrasonic power/data telemetry and neural stimulator with OOK-PM signaling," IEEE Transactions on Circuit and Systems—II: Express Briefs, vol. 60, No. 12, pp. 827-831, Dec. 2013.

S.-N. Suzuki et al., "Power and interactive information transmission to implanted medical device using ultrasonic," Japanese Journal of Applied Physics, vol. 41, part 1, No. 5B, pp. 3600-3603, May 2002.

Banerji et al "CMUT Ultrasonic Power Link Front-End for Wireless Power Transfer Deep in Body" 2013 IEEE MTT-S International Microwave Workshop Series . . . 2013.

* cited by examiner

WIDE BAND THROUGH-BODY ULTRASONIC COMMUNICATION SYSTEM

This application is the U.S. National Phase application under 35 U.S.C. § 371 of International Application No. PCT/EP 2015/070013, filed Sept. 2, 2015, which claims the benefit of EP Application Serial No. 14184338.3, filed Sept. 11, 2014. These applications are hereby incorporated by reference herein.

FIELD OF THE INVENTION

This invention relates to communication systems that use a liquid-like medium as the communication medium and, in particular, to a miniaturized wide band through-body ultrasonic communication system.

BACKGROUND OF THE INVENTION

It is frequently desirable to communicate with devices located inside the human body. For instance, it may be desirable to receive information from an implanted device such as a pacemaker or implanted cardiac defibrillator. A physician may want to know the status of the device such as battery charge or pulse delivery information. It may also be desirable to send information to the implanted device from outside the body such as to reprogram or change settings of the device. It may also be desirable to communicate with a catheter while it is located in a patient's vascular system such as during the placement of a stent by the catheter. Images or measurements may need to be supplied to the attending physician during a procedure, for instance. It may also be desirable to receive information from the tip of a needle during a biopsy or ablation procedure. The information to be communicated to the physician can include data regarding needle placement or the state of surrounding material. In an ablation procedure the receipt of temperature and tissue density information is important for determining the progress of the procedure. While this information can sometimes be communicated through wires in a catheter, biopsy needle or ablation device, the small size of a catheter, needle or ablation device often affords only limited space for communication lines, particularly where wiring is also needed for the functionality of the device itself. In such situations, wireless communication will obviate the need for communication conductors through the device. But common wireless techniques such as r.f. communication are often limited by the environment in which the communication must take place. Electrical or electromagnetic transmission can be highly attenuated by the body and can encounter interference from other medical equipment such as magnetic resonance systems and pacemakers, which create a noisy environment for through-body r.f. communication. Furthermore, r.f. and electromagnetic communication can be band-limited when operating through tissue. An implantable device using an ultrasonic transducer in kHz frequency range for wireless communication is known from WO 2008/011570. The data transfer rate of such devices is limited. Accordingly it is desirable to provide a wireless through-body communication system which can operate effectively from within the body and is not band-limited.

SUMMARY OF THE INVENTION

In accordance with the principles of the present invention, a wide band through-body communication system is described which communicates data through the body ultrasonically. Ultrasound within a band of useful frequencies is capable of passing through liquid-like media such as tissue without the limitations and restrictions encountered by r.f. and electromagnetic communication through the body. A preferred ultrasonic transducer for such communication is a MEMS or capacitive microelectronic ultrasonic transducer (CMUT) which can be controlled during manufacture and implementation to exhibit a broad bandwidth (larger than 80% for example) of operating frequencies. Most preferably the CMUT device is operated in a collapsed mode with its sensitivity and band of operation set by selection of an appropriate bias voltage for the device. For transmission the microelectronic CMUT device is operated by a microelectronic transmit circuit with an amplifier/driver and optional data encoder. For reception a microelectronic circuit is coupled to the CMUT to provide amplification of received signals and optional decoding. Preferably the CMUT device or devices are fabricated on the same die as the microelectronic communication circuitry. The assembly can be a dedicated transmitter or receiver or transceiver. In a constructed embodiment such assemblies have communicated up to 80 cm. through a liquid-like medium such as that presented by human tissue.

The present invention provides a unique combination of CMUT transducer characteristics, such as broad bandwidth and different operative frequencies, with microelectronic circuitry coding capabilities. The data transfer rate for the wide band through-body communication system in accordance to the present invention may reach as high as Mb/sec.

DETAILED DESCRIPTION OF THE EMBODIMENTS

With the increasing number and functionality of implantable medical devices, the need for a reliable high-throughput and safe through-body communication system is evident. There are several technological options that can serve this need such as r.f., magnetic or ultrasonic communication. The suitability of these approaches is judged by the properties of the communication channel (the human body) for the respective types of signals, the required size of the implementation and the achievable power/performance ratio. Further, for each type of signal there are safety limits for the signal amplitudes and duty cycles that can be used inside the body. Given these considerations, ultrasonic communication offers the best signal propagation for small form factors and energy consumption.

Ultrasonic communication is mechanical in nature. The electric signals that drive the acoustic transducers known as CMUTs cause mechanical movement of a membrane which in turn propagates pressure waves through the surrounding medium. The propagation properties depend on the properties of the sound wave in terms of pressure, frequency and on the properties of the propagation medium. In case of through-body propagation, different tissues propagate, reflect and absorb differently ultrasonic waves. An efficient transmission principle as described below is required to guarantee proper reception. Ultrasonic transducers can generate and receive modulated ultrasonic data signals. Ultrasonic transducers typically have a certain resonance frequency that depends on their physical size and implementation. A desirable CMUT implementation is capable of transmission with a center frequency of 4 to 8 MHz with greater than 80% or 100% bandwidth, the ratio of the operative frequency range of operation to the center frequency. This is in contrast to conventional piezo-electric transducers, which have a typical bandwidth of 10% to 50%. The broad bandwidth achievable with CMUT transducers allows transmission of wide band digital signals.

Figure 1:
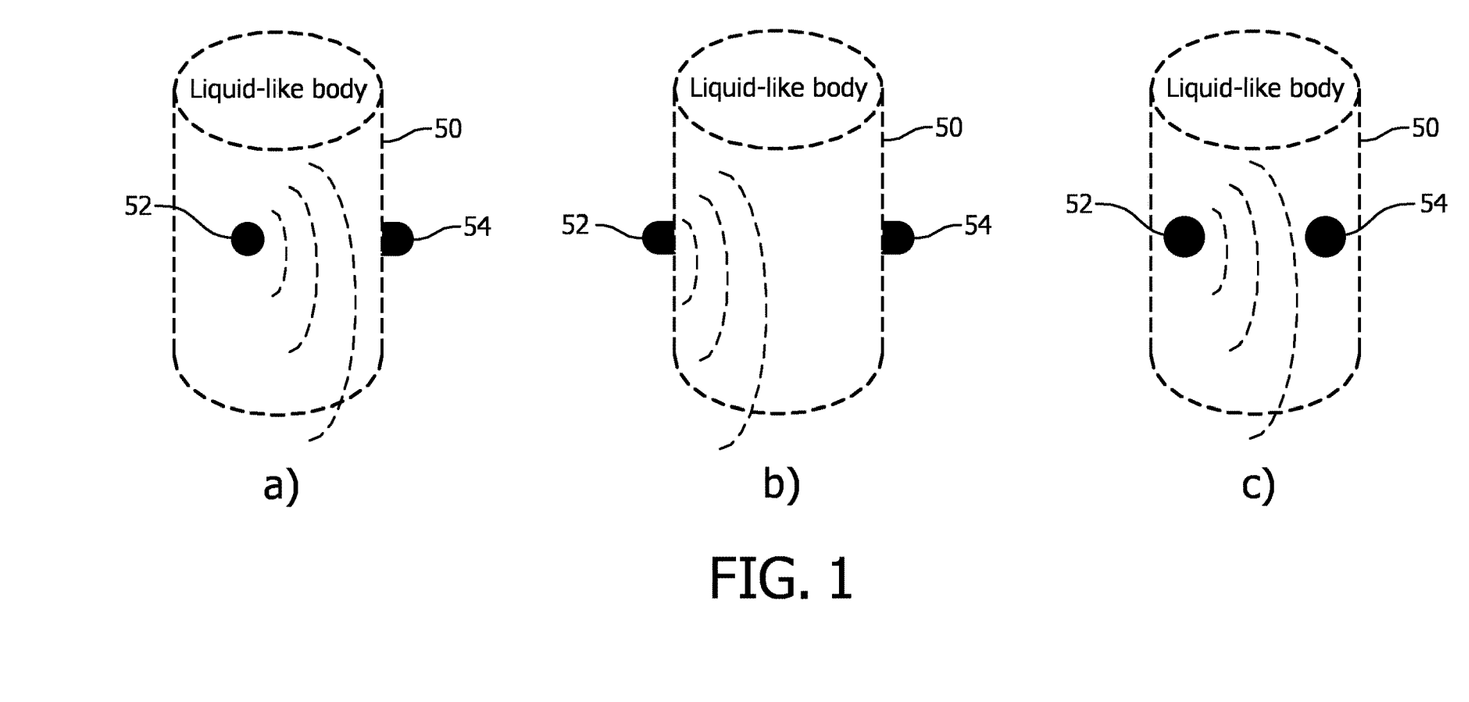
FIG. 1 illustrates several ways in which an ultrasonic communication system of the present invention can communicate through a liquid-like body such as the human body.

The ultrasonic transmission characteristics of the body lay in the frequency range of about 100 kHz up to about 40 MHz. Communication with lower ultrasonic frequencies, such as below 100 kHz, will suffer from poor spatial resolution (caused by the ultrasound wave diffraction) and increased size of the CMUT transducers. At higher frequencies the attenuation of the signals increases and thus the maximum communication distance that can be achieved with low power devices decreases. In ultrasonic through-body communication as described herein, the signals are transmitted via ultrasonic transducers, which are placed inside or in good acoustic contact with the surface of the body. As shown in FIG. 1, several application modalities can be defined with respect to the physical location of the transceivers relative to the communication medium. In FIG. 1a) an ultrasonic through-body communication device 52 within a liquid-like body 50 is transmitting through that medium to another ultrasonic through-body communication device 54 that is outside the body 50 and in acoustic contact with the body. In FIG. 1b) an ultrasonic through-body communication device 52 outside a liquid-like body 50 is in acoustic contact with and transmitting through the body medium to another ultrasonic through-body communication device 54 that is outside the body 50 and in acoustic contact with the body. In FIG. 1c) an ultrasonic through-body communication device 52 within a liquid-like body 50 is transmitting through that medium to another ultrasonic through-body communication device 54 that is also inside the liquid-like body 50. The ultrasonic through-body communication devices shown in FIG. 1 represent only the active transmitter/ receiver/transceiver with ultrasonic transducers as the antenna. In practice the communication devices can be stand-alone, battery-powered devices or can be attached to catheters and other instruments that connect them with external devices. In general, with devices of the present invention, data can be transferred from a device outside the body to a device inside of the body, from the inside to the outside of the body or from devices outside the body through the body and/or from devices inside the body to each other. The data communication is not limited to sending from a single transducer towards a single receiver but data can be sent from multiple transducers and be received by multiple receivers. The type of data is dependent on the specific application. In most implementations the data involves digital information.

Figure 2:
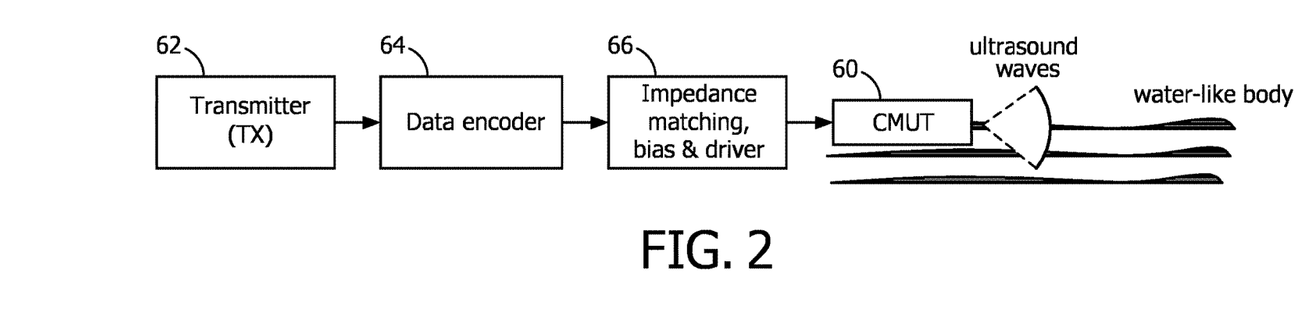
FIG. 2 illustrates a through-body ultrasonic transmit system constructed in accordance with the principles of the present invention.
Figure 3:
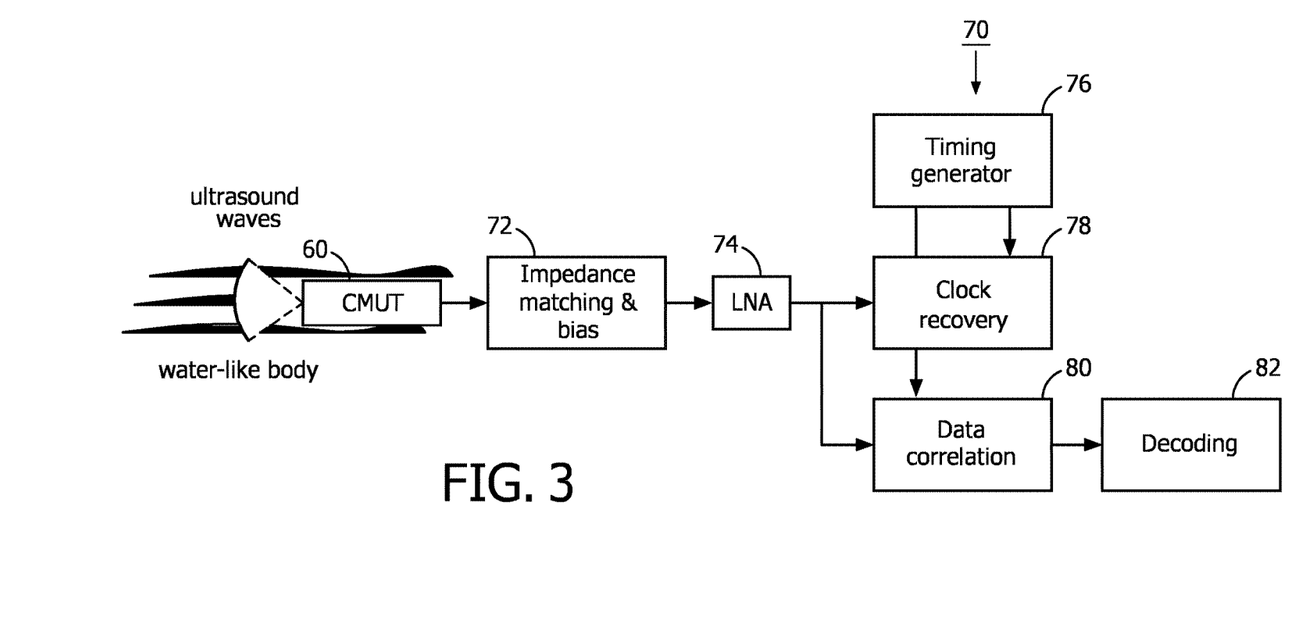
FIG. 3 illustrates a through-body ultrasonic receive system constructed in accordance with the principles of the present invention.
Figure 10:
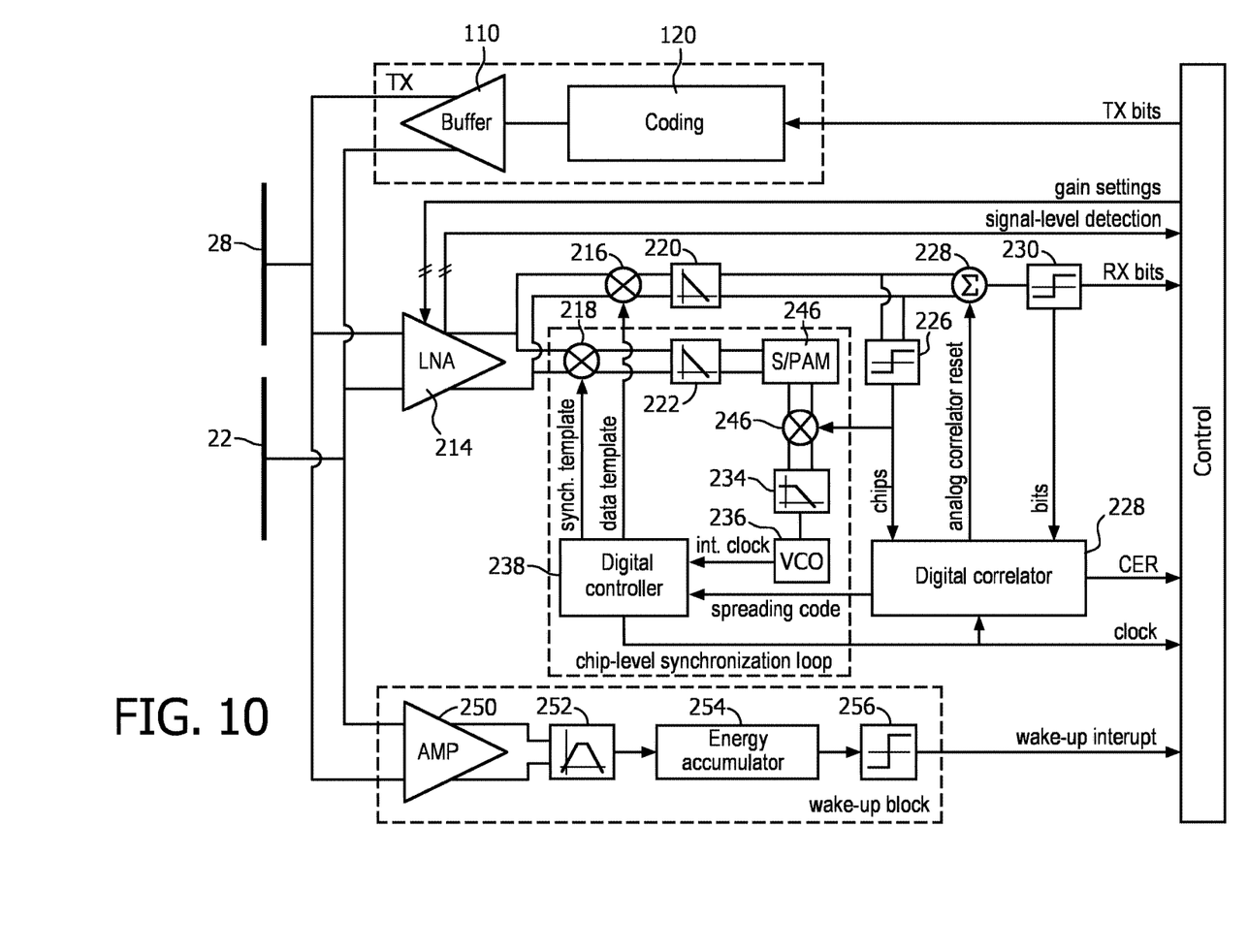
FIG. 10 is a block diagram of a microelectronic transceiver suitable for use in an ultrasonic CMUT communication system of the present invention.

FIGS. 2 and 3 illustrate block diagrams which describe the main components of a CMUT based ultrasonic communication channel, a transmit channel being illustrated in FIG. 2 and a receive channel illustrated in FIG. 3. The preferred operative frequency range of the channels is between 100 kHz to 40 MHz. FIG. 10 below illustrates these concepts combined in a transceiver configuration. As shown in FIG. 2, the data generated by a transmitter 62 is first encoded by a data encoder 64, which enables a DC-free coding. Manchester encoding is preferred in order to address the capacitive nature of the CMUT used for transmission, but another type of DC-free encoding may also be used. In a non DC free coding scheme the DC value of the encoded signal depends on the data being transmitted. Therefore, The DC-free coding addresses the capacitive nature of the CMUT transducer, since any additional DC signal may add to the bias voltage applied to the CMUT and cause an unwanted change in its operative frequency. In this implementation the encoded signal cannot be directly applied to the CMUT device 60. Since the CMUT 60 requires large voltage excitations in order to generate a sufficiently large acoustic signal, the encoded signal must first be amplified. In a constructed embodiment, a 200 mV (peak-peak) signal generated by the transmitter 62 is amplified by a 50 dB r.f. amplifier (driver). Furthermore, a bias voltage must also be applied in order to operate the CMUT device in the preferred collapsed mode. Communication may also be performed when the CMUT devices do not operate in collapsed mode, i.e., the uncollapsed or suspended mode. However, the resonant frequency in the uncollapsed mode is generally lower than in the collapsed mode and the low generated acoustic power could prevent effective operation of the communication link over the desired distance through the body. In the constructed embodiment, a bias voltage of about 100V is provided to the CMUT device to bias it to operate in the collapsed mode. A bias-T circuit was implemented in order to simultaneously provide the bias voltage and the a.c. drive voltage from a transducer driver to the CMUT device 60. Finally, the output impedance of the impedance matching, bias and driver/amplifier block 66 must be properly selected in order to enable the desired operation of the CMUT 60.

On the receive side shown in FIG. 3, a CMUT device 60 transforms the received acoustical signal into an electrical signal. An impedance matching circuit and a biasing voltage 72 are applied to the receiving CMUT device 60, similar to the transmit side. In the constructed embodiment, a bias-T circuit applied a bias voltage of about 100V to the CMUT device in order to set its sensitivity to the desired frequency range. The ultrasound wave picked up by the CMUT device 60 is thus transformed into an electrical signal. Since this signal is small, typically a few tens of mV peak-peak, a low noise amplifier (LNA) 74 first amplifies this signal before it is decoded. The impedance matching is done by selecting a LNA with a suitably large input impedance. The amplified signal is then provided to a receiver 70 which, in this embodiment, consists of the following elements. A clock recovery circuit 78 and a data correlation circuit 80 are coupled to receive the received communication signal and are responsive to a timing generator 76. The detailed operation of this circuitry is described in FIG. 10 below. The output of the data correlation circuit is then provided to a decoder 82, and the received data is then passed on to a utilization device such as a processor (not shown).

Figure 4:
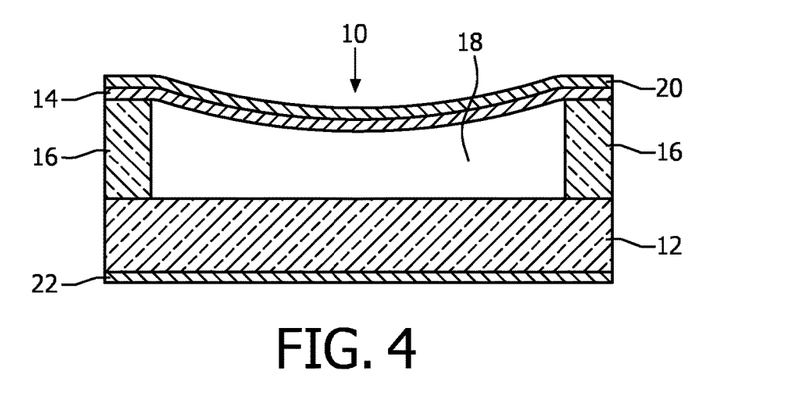
FIG. 4 is a cross-sectional view of a typical CMUT transducer cell.

Referring to FIG. 4, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied to the electrodes 20,22 will modulate the capacitance, causing the membrane to move and thereby transmit an acoustic signal.

Figure 5:
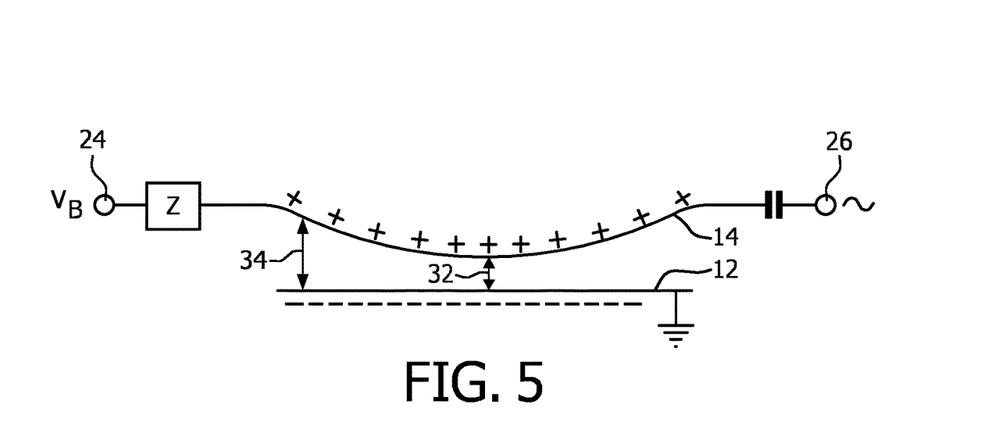
FIG. 5 is a schematic illustration of the electrical connections of a typical CMUT cell including an applied bias voltage.

FIG. 5 is an electrical schematic of the operation of the CMUT 10 of FIG. 4. A DC bias voltage VB is applied to a bias terminal 24 and is coupled to the membrane electrode 20 by a path which poses a high impedance Z to a.c. signals such as an inductive impedance. A.c. signals are capacitively coupled to and from the membrane electrode from a signal terminal 26. The positive charge on the membrane 14 causes the membrane to distend as it is attracted to the negative charge on the substrate 12. It has been found that the CMUT is most sensitive when the membrane is distended so that the two oppositely charged plates of the capacitive device are as close together as possible. A close proximity of the two plates will cause a greater coupling between acoustic and electrical signal energy by the CMUT. Thus it is desirable to increase the bias voltage VB until the dielectric spacing 32 between the membrane 14 and substrate 12 is as small as can be maintained under operating signal conditions. In constructed embodiments this spacing has generally been on the order of one micron or less.

Figure 6:
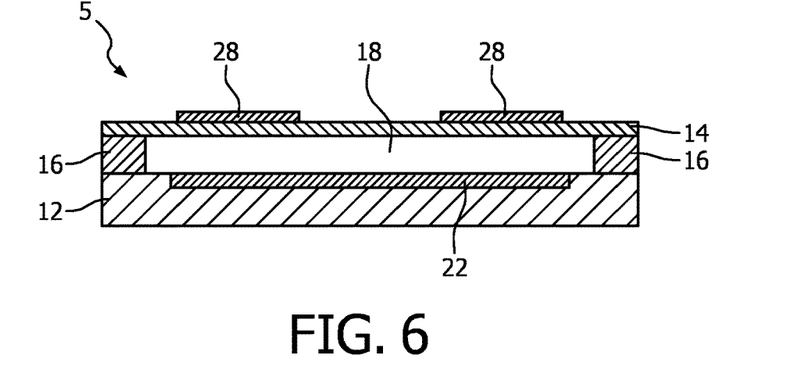
FIG. 6 is a cross-sectional view of a CMUT cell constructed for collapsed mode operation in accordance with the principles of the present invention.

With reference to FIG. 6, a schematic cross-section of a CMUT element 5 suitable for operation in the collapsed mode is depicted. CMUT element 5 includes a substrate layer 12, an electrode 22, a membrane layer 14, and a membrane electrode ring 28. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. The cell and its cavity 18 may define alternative geometries. For example, cavity 18 could define a rectangular and/or square cross-section, a hexagonal cross-section, an elliptical cross-section, or an irregular cross-section. The bottom electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduces charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with collapsed mode CMUTs, which are more susceptible to charge retention than an uncollapsed device. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 6, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

Figure 7:
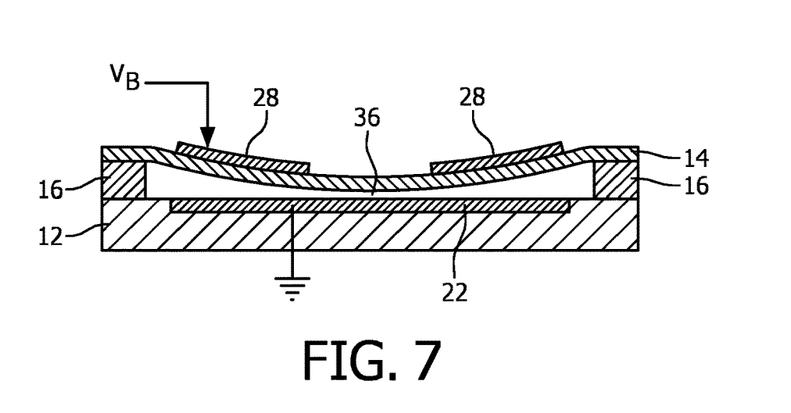
FIG. 7 illustrates the CMUT cell of FIG. 6 when biased into a collapsed state.

FIG. 7 shows the CMUT cell of FIG. 6 when biased to a precollapsed state, in which the membrane 14 is in contact with the floor of the cavity 18. This is accomplished by applying a DC bias voltage to the two electrodes as indicated by voltage $V_B$ applied to the electrode ring 28 and a reference potential (ground) applied to the substrate electrode 22. While the electrode ring 28 could also be formed as a continuous disk without the hole in the center, FIG. 7 illustrates why this is not necessary. When the membrane 14 is biased to its precollapsed state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the disk or ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved. In the collapsed mode the resonance frequency of the CMUT cell increases with an increase of the bias voltage provided by the bias circuit.

Figure 8:
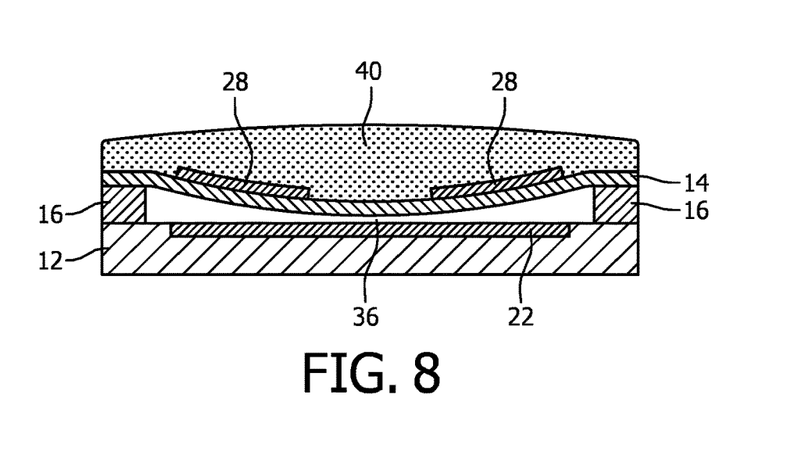
FIG. 8 illustrates the CMUT cell of FIG. 6 when the cell membrane is retained in the collapsed state by a lens fabricated on top of the cell.

The membrane 14 may be brought to its precollapsed state in contact with the floor of the cavity 18 as indicated at 36 by applying the necessary bias voltage, which is typically in the range of 50-100 volts. As the voltage is increased, the capacitance of the CMUT cell is monitored with a capacitance meter. A sudden change in the capacitance indicates that the membrane has collapsed to the floor of the cavity. The membrane can be biased downward until it just touches the floor of the cavity as indicated at 36, or can be biased further downward to increased collapse beyond that of minimal contact. The advantage of the collapsed operation mode the operative frequency of the CMUT cell (transducer) can be varied with bias voltage FIG. 8 illustrates another technique for biasing the membrane 14 to a precollapsed state, which is by means of a retention member 40. While the membrane 14 is electrically biased to its precollapsed state as shown in FIG. 7, a retention member 40 is placed or formed above the membrane which physically retains the membrane in its precollapsed state. In a preferred embodiment for an ultrasound transducer which performs imaging, the structure forms the lens of the transducer. A transducer lens normally fulfills three requirements. One is that the lens provides a structure which endures wear resistance due to the frictional contact produced during use of a transducer probe. In effect, the lens provides a physical cover which protects a underlying transducer array comprising ultrasound transducers from physical wear. Second, a lens is nonconductive and thereby provides electrical insulation between the electrical elements of the transducer and the patient. This is an important characteristic for an in-body communication device such as the devices of the present invention. Third, a lens can provide focal properties for the probe. In the example of FIG. 8, the retention member 40 provides a fourth benefit, which is to physically retain the membrane 14 in its precollapsed state.

Various materials may be used for the retention member. The only requirement for the CMUT is that the material be of sufficient stiffness to retain the membrane in its collapsed state after the bias voltage is removed. One suitable material is polydimethyl siloxane (PDMS or RTV rubber). The RTV material is cast over the CMUT while the bias voltage $V_B$ holds the membrane in its desired collapsed state. After the RTV polymerizes and is sufficiently stiff to physically retain the membrane in its precollapsed state, the bias voltage can be removed and does not need to be reapplied until the device is biased for operation. Preferably the retention member is bonded to the areas around each membrane of the CMUT array. Other materials which may be suitable for the retention member 40 include urethane rubber, vinyl plastisols, and thermoplastic elastomers.

By physically retaining the membrane in its precollapsed state, no bias is necessary to maintain the precollapsed condition until the operating bias is applied during use of the device. This means that the CMUT can be operated at lower voltages, which is advantageous for miniaturized devices such as in-body communication devices. Furthermore, adverse effects due to variability in manufacturing and material characteristics, such as variation in membrane size, stiffness or cavity depth from lot to lot can be eliminated. These variabilities may mean that more or less bias voltage is needed to bring the CMUT to its precollapsed state. The bias voltage is adjusted accordingly to the desired degree of collapse, and then the retention member holds the membrane in this state. Thus, each CMUT array can be set up for the same performance characteristics or its coupling customized even in the presence of these tolerance variations. Greater uniformity of the probes in terms of characteristics such as operating voltage range, acoustic impedance, capacitance, and coupling coefficient can be achieved.

Figure 9:
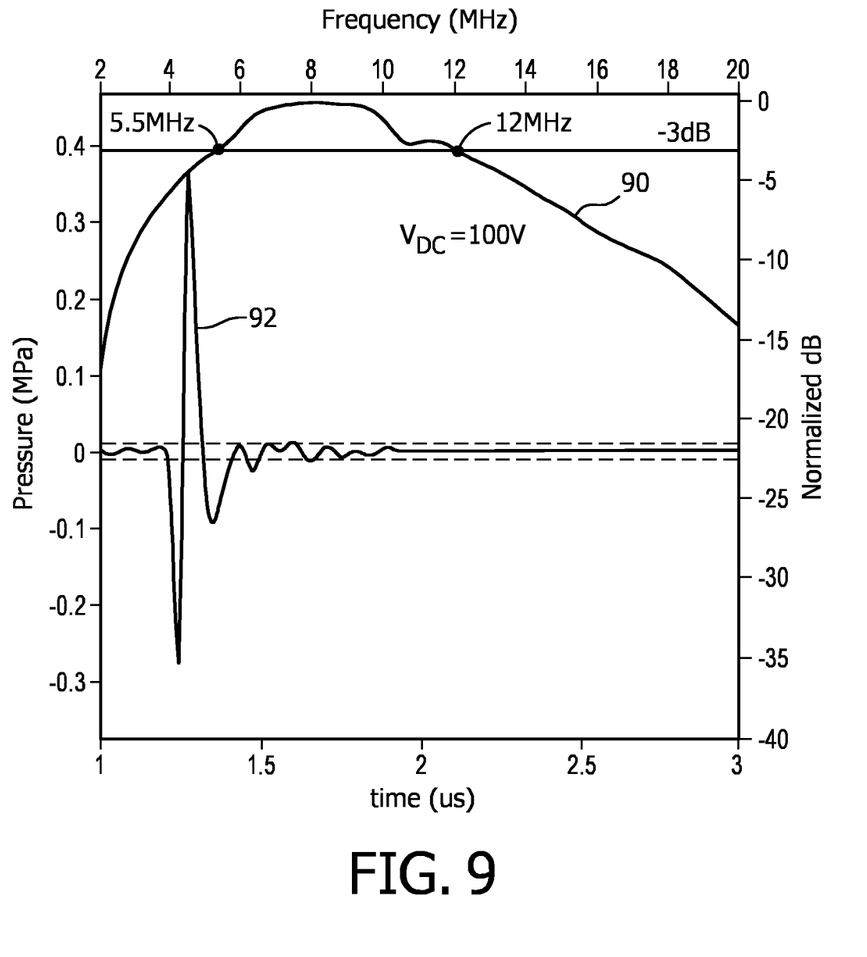
FIG. 9 illustrates a typical wide band response characteristic of an ultrasonic CMUT communication system of the present invention.

FIG. 9 is a plot of the typical broad band performance of a collapsed mode CMUT transducer such as those shown in FIGS. 7 and 8. For an applied or received impulse 92, a typical collapsed mode CMUT transducer will exhibit a frequency response as shown by curve 90. As the 3 dB points of this curve illustrate, for frequencies in the 4 to 8 MHz range the bandwidth of the collapsed mode CMUT transducer approaches or exceeds 100%, making it ideal for a wide band communication system.

FIG. 10 illustrates a transceiver system for a through-body ultrasonic communication system of the present invention. The transmitter subsystem TX of the transceiver comprises a coder or coding circuit (C) 120 which codes a bit stream BS of TX bits to be transmitted in another digital bit stream according to a selected spreading code and according to the requirement of having at least one signal transmission for each transmitted bit (transmission period). Then this bit stream is coupled to the body via a digital buffer 110, which may also boost the signal to levels required by the subsequent CMUT driver. If needed, the digital buffer 110 could also provide bandwidth limitation.

In the receiver subsystem, an input amplifier (e.g., low noise amplifier (LNA)) 214 is DC decoupled to the CMUT electrodes 22, 28 The amplified signal of the CMUT (or CMUTs) is then fed to two correlator circuits used for data detection and synchronization. In the illustrated example, both correlators are implemented by analog multiplication of digital templates (e.g., a 1-bit-template "synch. template" as a synchronization pattern for the synchronization and a 1-bit-template "data template" as a reference signal for the data detection), with the incoming signal in respective data or synchronization multipliers 216, 218. When the synchronization template is "1" the amplified signal is multiplied by "1" (i.e., by a positive, constant, multiplication factor) by the synchronization multiplier 218. When the synchronization template is "0", the amplified signal is multiplied by "−1" (i.e., by a negative, constant, multiplication factor) by the synchronization multiplier 218. The results of the multiplications are then integrated in respective data or synchronization integrators 220, 222 over the reception period (e.g., the chip period) to actually compute the respective data or synchronization correlation. The integration outputs correspond to the desired data and synchronization information.

In order to close the chip-level synchronization loop shown in the dashed box, the correlation between the synchronization template and the incoming signal is sampled at the end of the integration period by a sampling and pulse amplitude modulation (PAM) circuit (S/PAM) 224. The integrated output of the correlator is a measure of the difference between the incoming signal frequency and the local template. The smaller the output (i.e., the better the correlation), the smaller the synchronization error. After the error is lower than the sensitivity threshold, the reception is considered synchronized and the second data correlation starts The sampled PAM value can now be multiplied in a further multiplier 246 by "+1" or "−1" according to the polarity of the detected data ("chips") in order to guarantee the right polarity according to the incoming data. During the synchronization sequence the polarity selection can be performed by using a fixed synchronization pattern compliant with the synchronization sequence generated by the transmitter subsystem. The further multiplier 246 thus acts as a polarity control element which controls the polarity of the output value of the second correlator in accordance with the polarity of the detected data (i.e., decoded signal). The signal from the multiplier 246 is filtered in a loop-filter 234 and fed to a voltage-controlled oscillator (VCO) 236 that generates, based on its input, an internal clock (int. clock) used as a time base or time reference for the generation of the control and template signals by the digital controller 238. The filtering of the synchronization information is thus performed by generating a pulse (PAM signal) proportional to the sampled signal that is then filtered by the loop filter 234.

In the data detection branch, the correlation at the data correlator is performed at chip-level and can be first converted to a digital bit stream ("chips") by using a comparator or threshold circuit 226 and fed to a digital correlator 232 that performs a symbol level synchronization and provides a correct and synchronized code sequence ("spreading code") for template generation by the digital controller 238. If analog correlation at symbol level is also required for reliability reasons, the analog output of the chip level correlator can be further integrated over the symbol length by an analog accumulator 228 and the digital correlator 232 can control the accumulation time over the symbols by generating an analog correlator reset signal and supplying it to the analog accumulator 228. The symbol-level correlation is then converted to digital by using a comparator or threshold circuit 230 to provide the desired bit stream RX bits. If reliability is not a problem the analog accumulator can be omitted and the digital correlator can be used for symbol level correlation.

As an additional option, a comparison between the output bit stream RX bits, coming from the analog symbol-level correlator and an expected bit stream generated by the digital correlator, could be used as a measure of the quality of the incoming signal, which could be presented as Chip-Error-Rate signal CER.

The transceiver of FIG. 10 also includes an ultra-low-power wake-up detector that can sense the channel in idle mode. This allows for switching off the power-consuming main receiver block. When communication is detected in the channel, the main receiver block is switched on to start receiving the data. The wake-up detector consists of a (low-noise) amplifier input stage 250 followed by a narrow band-pass filter 252 set to the communication band, an energy accumulator 254, and a comparator or threshold circuit 256. The wake-up detector, upon detecting a received signal, activates the main receiver with a wake-up interrupt coupled to the processor ("CONTROL") which operates the transceiver and processes the information signals it produces.

It is worth noting that several additions to this structure can be made. As an example, a rotational frequency detector can be added that applies a one-bit analog-to-digital conversion to the outputs of the chip-level analog correlators (one for the data branch and one for the synchronization branch). The obtained two-bit information can be used to detect the sign of the frequency difference between the receiving side and the transmitting side by monitoring its evolution over time. This information can be used to increase the pull-in range of the synchronization system and therefore allow synchronization even without an accurate time reference such as a crystal oscillator or the like.

A through-body ultrasonic communication device of the present invention can exhibit the following advantages:

1) An ultrasonic communication link of the present invention is able to achieve high data throughout due to the usage of a broadband transducer (such as a CMUT) in combination with a broadband transceiver architecture.

2) Small size transceiving elements can be used. When MEMS devices such as CMUTs are used, the CMUT transceiving elements can be integrated on the same die as the micro-electronic transceiver circuit. Thus, a form factor of a few square millimeters can be achieved.

3) The weak acoustic scattering in soft tissue allows robust signal propagation that can be used for data communication. As in water, ultrasound propagates much better through the body than r.f. or electromagnetic waves. Thus, a communication link of the present invention can achieve Mb/sec. data transfer rate with very low energy consumption and low energy induction in the body.

4) Ultrasonic through-body communication devices of the present invention avoid interference with electric medical systems (e.g., magnetic resonance imaging, pacemaker, etc.) and their high immunity to acoustic noise and interference provides robustness in the presence of other medical devices used concurrently (e.g., for imaging). Interference mitigation inside or close to the operation frequency band is generally not needed.

5) An implementation of the present invention offers high immunity to noise and interference and thus allows for communication with very low signal levels. The ultrasound can be transmitted in a specific direction toward a receiver. In case ultrasonic through-body communication device comprises several CMUT transducers in an array. The aperture can be designed to produce an acoustic beam with a specific width and angle (similar to the ultrasound imaging). This can be used to transmit the data towards a specific receiver (out of several). Also, the receiver can be tuned to listen to a specific or multiple transmitters. Another option is to transmit/receive the ultrasound in multiple angles. This improves the energy efficiency and the robustness of the communication link.

6) As compared with devices of the prior art, an implementation of the present invention allows for communication between two or more through-body communicating devices and also allows for bi-directional communication between two ultrasonic transducers of such devices.

7) Energy consumption is minimized by the use of wake-up circuitry for the receiver.

The constructed embodiment described above has proven that through-body ultrasonic communication is possible over distances of at least 30 cm.

Through-body communication devices of the present invention may be used in the following applications, among others.

A. Pacemakers

An ultrasonic transceiver, typically employing a CMUT device connected to a wideband communication transceiver such as shown in FIG. 10 can be implemented in a pacemaker. Several functions can thus be enabled, such as configuring the pacemaker after being implanted in the patient. Another function is to enable the pacemaker to provide information on its current status (e.g., the status of its internal battery and pulse rate delivered. Thus, an easy way of checking the correct operation of the pacemaker is provided.

Moreover, as mentioned earlier, the communication link between an ultrasonic transceiver incorporated in the pacemaker and an externally applied on-body ultrasonic transceiver is not affected by interferences from other electrical medical systems (e.g., a magnetic resonance imaging system). Thus, a robust communication link is also achievable in a hospital environment.

The ultrasonic communication device implemented in the pacemaker can be designed such that it operates at a low bias voltage. Lithium-ion batteries are typically used in implants such as pacemakers. This type of battery provide a supply voltage typically in the range of 1-5 volts. Thus, the CMUT device integrated in the implant must be able to correctly operate at such low a.c. voltages; that is, it must be able to generate sufficient acoustical energy in the appropriate frequency bandwidth (i.e., the frequency bandwidth of the transceiver). These characteristics (frequency bandwidth, bias voltage, etc.) can be set when designing the CMUT device as described in international patent publication WO 2010097729 A1. Alternatively, a local boost of the bias voltage to a few tens of volts can be realized electronically with voltage boosters.

The pacemaker embodiment comprises of an ultrasonic through-body communication system comprising:
 a pacemaker which is implanted in a body;
 an ultrasonic through-body communication device, incorporated into the pacemaker, and comprising:
 an ultrasonic transducer which transmits or receives data encoded in ultrasonic waves passing through the body;
 a transducer driver and an amplifier coupled to the ultrasonic transducer; and
 a transceiver coupled to the transducer driver, the amplifier, and the pacemaker;
 wherein the ultrasonic through-body communication device transmits and receives data through the body surrounding the pacemaker.

In this embodiment the ultrasonic transducer further may comprise a CMUT transducer. The ultrasonic through-body communication system further comprising a battery providing voltage in the range of 1-5 volts to power the ultrasonic through-body communication device. Moreover, the data further comprises one of pacemaker configuration data or battery status data.

B. Intravascular Catheters

Another use of devices of the present invention lies in the field of endocavity ultrasound imaging, in particular intravascular ultrasound (IVUS), where catheters with a miniaturized ultrasound transducer array are used to image the inner walls of blood vessels. Ultrasound imaging system comprises an array of the ultrasound transducers coupled to integrated circuitry enabling ultrasound beamforming capabilities. The IVUS catheters are commonly used in stent placement procedures. IVUS catheters need to be as thin as possible, in order to be able to reach narrow veins and thinner catheters give rise to a broader range of applications and procedures.

In an IVUS catheter, the imaging data captured by the ultrasound transducer is transported electronically by wires through the catheter and to an imaging system where it is processed and displayed. The more elements the transducer has, the better the ultrasound image can be. Since the data of every ultrasound element needs to be processed and send through the catheter, a compromise is made between the amount of wires running through the catheter and the amount of multiplexing of the data at the catheter tip before sending it through the catheter. Multiplexing in the catheter is, however, limited due to heat generation and size restrictions. Use of an ultrasound communication link to transmit the imaging data to a receiver on the outside of the body provides an attractive method to limit the amount of wires in the catheter while still providing good image quality. Ultrasound imaging is commonly performed in a range of ultrasound frequencies from 1 MHz up to 40 MHz. Therefore, the present invention allows an implementation of the communication device into the ultrasound imaging system such that the same CMUT elements used for ultrasound imaging in the array can be also used as the data communication transducers. In this embodiment imaging and communication can be performed in a time-interleaved manner. Other implementations include using several elements to image and others to communicate at the same time and using different frequencies for imaging and communication. The advantage of such an ultrasound system is the present invention enables double capability of the CMUT element: ultrasound imaging and wireless data exchange using ultrasound. The operative (or resonance) frequency of the element can be tuned by the applied bias voltage expanding the transducer's band-width and sensitivity.

The intravascular catheter embodiment comprise an ultrasonic through-body communication system comprising:
 a catheter which is introduced into a body by means of the vascular system of the body; and
 an ultrasonic through-body communication device, incorporated into the catheter, and comprising:
 a CMUT transducer transmits or receives data encoded in ultrasonic waves passing through the body;
 a transducer driver coupled to the ultrasonic transducer; and
 a transmitter coupled to the transducer driver and the catheter;
 wherein the ultrasonic through-body communication device transmits data through the body surrounding the catheter.

In yet another embodiment the catheter further comprises an ultrasonic imaging transducer,
 wherein the ultrasonic transducer of the ultrasonic through-body communication device further comprises the ultrasonic imaging transducer of the catheter.

In addition the data may further comprise ultrasonic image data acquired by the ultrasonic imaging transducer of the catheter.

C. Intervention Procedures

Another use of devices of the present invention is in intervention procedures employing devices that are temporarily inserted in the human body in order to extract biological material (e.g. biopsy procedures), to apply medical substances like anesthesia or drug delivery, or perform thermal ablation. These devices can be extremely small (e.g., needles) and require very high positioning accuracy such that the substances can be extracted or applied to very small targeted regions in the body. These process can be facilitated by technologies that determine the location of a needle tip or ablator inside the body and the nature of the immediate surroundings such as its temperature or tissue density. Further, these devices can benefit from control signals that can adjust their functions. As the needles might be too small to incorporate cables, those systems can benefit from wireless communication that is suitable for in-body operation like that provided by the ultrasonic communication devices of the present invention. As ultrasonic communication with CMUTs can be realized with a very small form factor, such a communication device can be integrated in a needle or another device that is temporarily inserted in the body. The communication can be used as a localization beacon, settings transfer or for transmitting local parameters of the environment.

The interventional embodiment comprises an ultrasonic through-body communication system comprising:
 an interventional device which is introduced into a body; and
 an ultrasonic through-body communication device, incorporated into the interventional device, and comprising:
 an ultrasonic transducer which transmits data encoded in ultrasonic waves passing through the body;
 a transducer driver coupled to the ultrasonic transducer; and
 a transmitter coupled to the transducer driver and the interventional device;
 wherein the ultrasonic through-body communication device transmits and receives data through the body surrounding the interventional device.

In this embodiment the interventional device may further comprises a biopsy needle and/or an ablation device; and the ultrasonic transducer may further comprise a CMUT transducer.

The invention claimed is:

1. An ultrasonic through-body communication device comprising:
   a transmitter adapted to provide data for transmission to a receiver;
   a data encoder adapted to receive the data provided by the transmitter, wherein the data encoder performs a DC-free data encoding of the data into an encoded data signal;
   a transducer driver adapted to receive the encoded data signal, wherein the transducer driver is adapted to provide an amplified drive signal comprising the encoded data signal;
   a CMUT transducer adapted to operate at an ultrasonic frequency band and responsive to the amplified drive signal, wherein the CMUT transducer is adapted to be acoustically coupled to a water-like body to transmit broadband ultrasonic data signals comprising the encoded data signal through the body for reception by the receiver, wherein the ultrasonic frequency band at which the broadband ultrasonic data signals are transmitted comprises frequencies between 100 kHz to 40 MHz; and
   a bias circuit adapted to provide a bias voltage to collapse the CMUT transducer such that the CMUT transducer operates in a collapsed mode to wirelessly transmit the broadband ultrasonic data signals to the receiver at a data transfer rate of at least 1 Mb/sec.

2. The ultrasonic through-body communication device of claim 1, further comprising:
   an impedance matching circuit, coupled between the transducer driver and the CMUT transducer.

3. The ultrasonic through-body communication device of claim 1, wherein the CMUT transducer is adapted to transmit broadband ultrasonic data signals with a bandwidth greater than 100%.

4. The ultrasonic through-body communication device of claim 1, wherein the ultrasonic frequency band comprises frequencies between 4MHz to 8 MHz.

5. The ultrasonic through-body communication device of claim 1, wherein the data encoder is configured to apply a Manchester encoding to the data provided by the transmitter.

6. The ultrasonic through-body communication device of claim 1, further comprising a battery configured to provide a voltage to at least one of the transmitter, data encoder, transducer driver, CMUT transducer, or the bias circuit, wherein the voltage is between approximately 1V and approximately 5V.

7. The ultrasonic through-body communication device of claim 1, wherein the transmitter, data encoder, transducer driver, CMUT transducer, and bias circuit are positioned at a distal portion of an intravascular imaging catheter, and wherein the data provided for transmission to the receiver comprises ultrasound imaging data.

8. The ultrasonic through-body communication device of claim 1, wherein the transducer driver is configured to provide the amplified drive signal at the ultrasonic frequency band.

9. An ultrasonic through-body communication device comprising:
   a CMUT transducer adapted to be acoustically coupled to a water-like body and to receive broadband ultrasonic data signals which have traveled through the body from a transmitter, the broadband ultrasonic data signals comprising an encoded data signal, wherein the broadband ultrasonic data signals are transmitted at a frequency band between 100 kHz up to about 40 MHz, and wherein the broadband ultrasonic data signals are received by the CMUT transducer by applying a bias voltage to collapse the CMUT transducer such that the CMUT transducer operates in a collapsed mode to wirelessly receive the broadband ultrasonic data signals from the transmitter at a data transfer rate of at least 1 Mb/sec;
   a bias circuit coupled to the CMUT transducer to provide the bias voltage;
   an amplifier, coupled to the CMUT transducer and adapted to amplify the received broadband ultrasonic data signals;
   a receiver adapted to receive the amplified broadband ultrasonic data signals and to extract the encoded data signal from the received broadband ultrasonic data signals; and
   a decoder adapted to decode an information data signal from the encoded data signal using a DC-free data encoding.

10. The ultrasonic through-body communication device of claim 9, wherein the receiver is further configured to perform data correlation.

11. The ultrasonic through-body communication device of claim 9, further comprising:
   an impedance matching circuit, coupled between the CMUT transducer and the amplifier.

12. The ultrasonic through-body communication device of claim 9, wherein the receiver further comprises:
   a wake-up circuit, responsive to ultrasonic signals of a desired frequency, which causes the receiver to become fully actuated to process the received broadband ultrasonic data signals.

13. An ultrasonic through-body communication transceiver comprising:
   a CMUT transducer adapted to be acoustically coupled to a water-like body, wherein the CMUT transducer is further adapted to transmit first broadband ultrasonic data signals through the body and to receive second broadband ultrasonic data signals from a transmitter which have traveled through the body, wherein the CMUT transducer transmits the first broadband ultrasonic data signals a frequency band between 100 kHz up to about 40 MHz;
   a transmitter providing data to a receiver;
   a data encoder adapted to receive the data provided by the transmitter, wherein the data encoder performs a DC-free data encoding of the data into an encoded data signal;
   a transducer driver adapted to receive the encoded data signal, wherein the transducer driver is adapted to provide an amplified drive signal to the CMUT transducer;
   a bias circuit coupled to the CMUT transducer to provide a bias voltage to collapse the CMUT transducer to operate in a collapsed mode to wirelessly transmit the first broadband ultrasonic data signals at a data transfer rate of at least 1 Mb/sec;
   an amplifier, coupled to the CMUT transducer, which amplifies the received second broadband ultrasonic data signals;

a receiver adapted to receive the amplified second broadband ultrasonic data signals and to extract the encoded data signal from the received second broadband ultrasonic data signals; and a decoder adapted to decode information data signals from the encoded data signal using the DC-free data encoding.

14. The ultrasonic through-body communication transceiver of Claim 13, wherein the CMUT transducer is a transducer of an ultrasound imaging system providing ultrasonic imaging data and the first broadband ultrasonic data signals comprise the ultrasonic imaging data.

* * * * *